(12) United States Patent
Cho et al.

(10) Patent No.: US 12,025,580 B2
(45) Date of Patent: Jul. 2, 2024

(54) ION DETECTION SENSOR FABRICATION METHOD AND ION DETECTION SENSOR FABRICATED BY THE SAME

(71) Applicant: MCK TECH CO., LTD., Daejeon (KR)

(72) Inventors: Seung Min Cho, Seongnam-si (KR); Min Gu Cho, Goyang-si (KR); Ki Soo Kim, Seongnam-si (KR); Hong Gi Oh, Daegu (KR)

(73) Assignee: MCK TECH CO., LTD., Daejeon (KR)

( * ) Notice: Subject to any disclaimer, the term of this patent is extended or adjusted under 35 U.S.C. 154(b) by 401 days.

(21) Appl. No.: 17/621,229

(22) PCT Filed: Oct. 18, 2021

(86) PCT No.: PCT/KR2021/014453
§ 371 (c)(1),
(2) Date: Dec. 20, 2021

(87) PCT Pub. No.: WO2022/092656
PCT Pub. Date: May 5, 2022

(65) Prior Publication Data
US 2022/0349853 A1    Nov. 3, 2022

(30) Foreign Application Priority Data
Oct. 30, 2020 (KR) .......................... 10-2020-0142798

(51) Int. Cl.
*G01N 27/414* (2006.01)
(52) U.S. Cl.
CPC ................................. *G01N 27/414* (2013.01)

(58) Field of Classification Search
None
See application file for complete search history.

(56) References Cited

U.S. PATENT DOCUMENTS

| 2015/0287543 A1* | 10/2015 | Aksay | .................... B82Y 40/00 |
| | | | 252/182.1 |
| 2019/0204252 A1* | 7/2019 | Venugopal | ............ C23C 16/047 |

(Continued)

FOREIGN PATENT DOCUMENTS

| JP | 2020-153695 A | 9/2020 |
| KR | 10-2015-0004254 A | 1/2015 |

(Continued)

OTHER PUBLICATIONS

International Search Report of PCT/KR2021/014453 mailed Feb. 7, 2022.

(Continued)

*Primary Examiner* — Benjamin P Sandvik
(74) *Attorney, Agent, or Firm* — Revolution IP, PLLC

(57) ABSTRACT

An ion detection sensor fabrication method includes: preparing an ion-sensitive film preparation solution; preparing an ion-sensitive mixed layer preparation solution by mixing the ion-sensitive film preparation solution with graphene powder; and forming an ion-sensitive mixed layer sensitive to a target ion by applying the ion-sensitive mixed layer preparation solution to fill a gap between a source and a drain spaced apart from each other and to cover at least a portion of an upper surface of each of the source and the drain.

8 Claims, 5 Drawing Sheets

(56) References Cited

U.S. PATENT DOCUMENTS

2019/0293595 A1* 9/2019 Walsh ................ G01N 27/3335
2021/0239646 A1* 8/2021 Hwang ............. H01L 21/02282
2022/0404301 A1* 12/2022 Pan ...................... G01N 27/327

FOREIGN PATENT DOCUMENTS

| KR | 10-2019-0019013 A | 2/2019 |
| KR | 10-2019-0083120 A | 7/2019 |
| WO | 2018-208742 A1 | 11/2018 |

OTHER PUBLICATIONS

Office Action of Korean Patent Application No. 10-2020-0142798 mailed Oct. 13, 2022.
Amr M. Marhmoud et al., "Design of Solid-contact Ion-selective Electrode with Graphene Transducer Layer for the Determination of Flavoxate Hydrochloride in Dosage Form and in Spiked Human Plasma", Electroanalysis, Aug. 28, 2020, vol. 32, pp. 2803-2811.

* cited by examiner

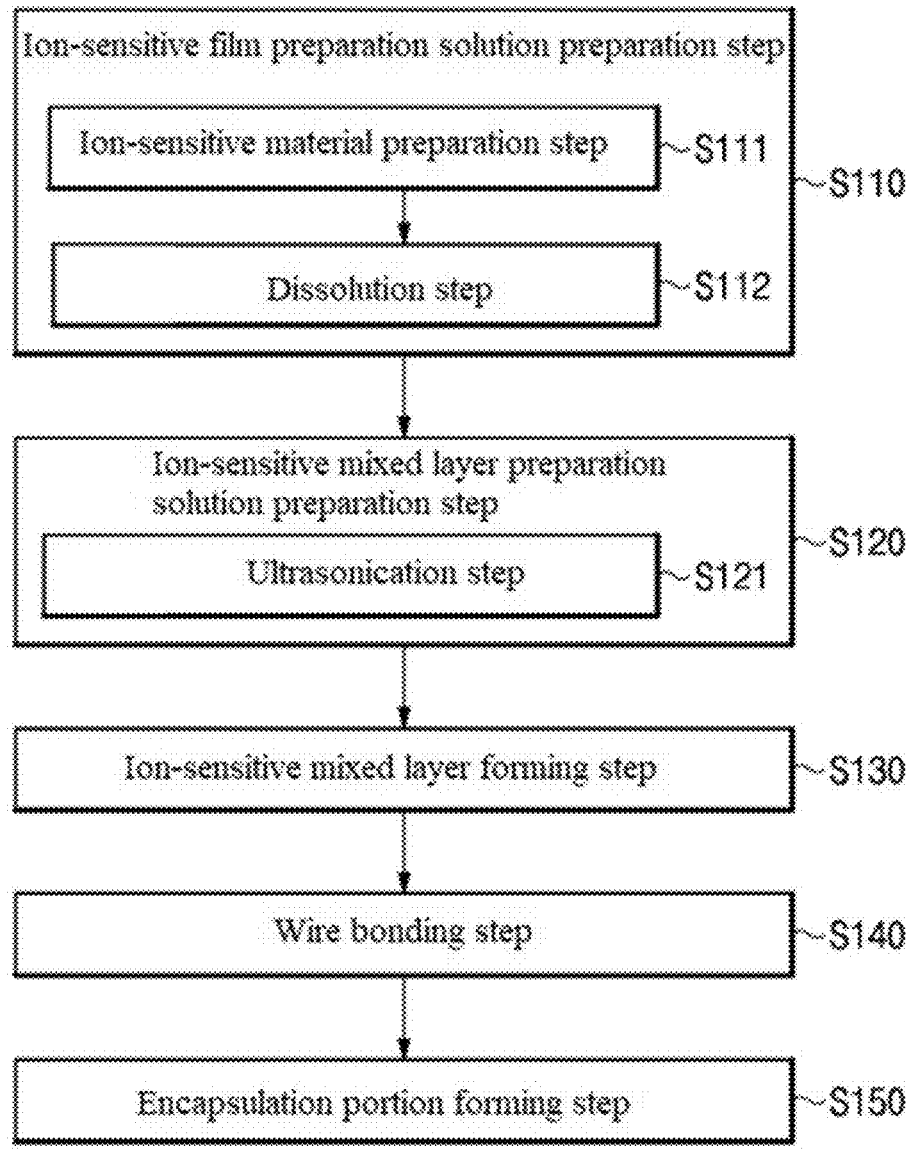
[FIG. 1]

[FIG. 2]
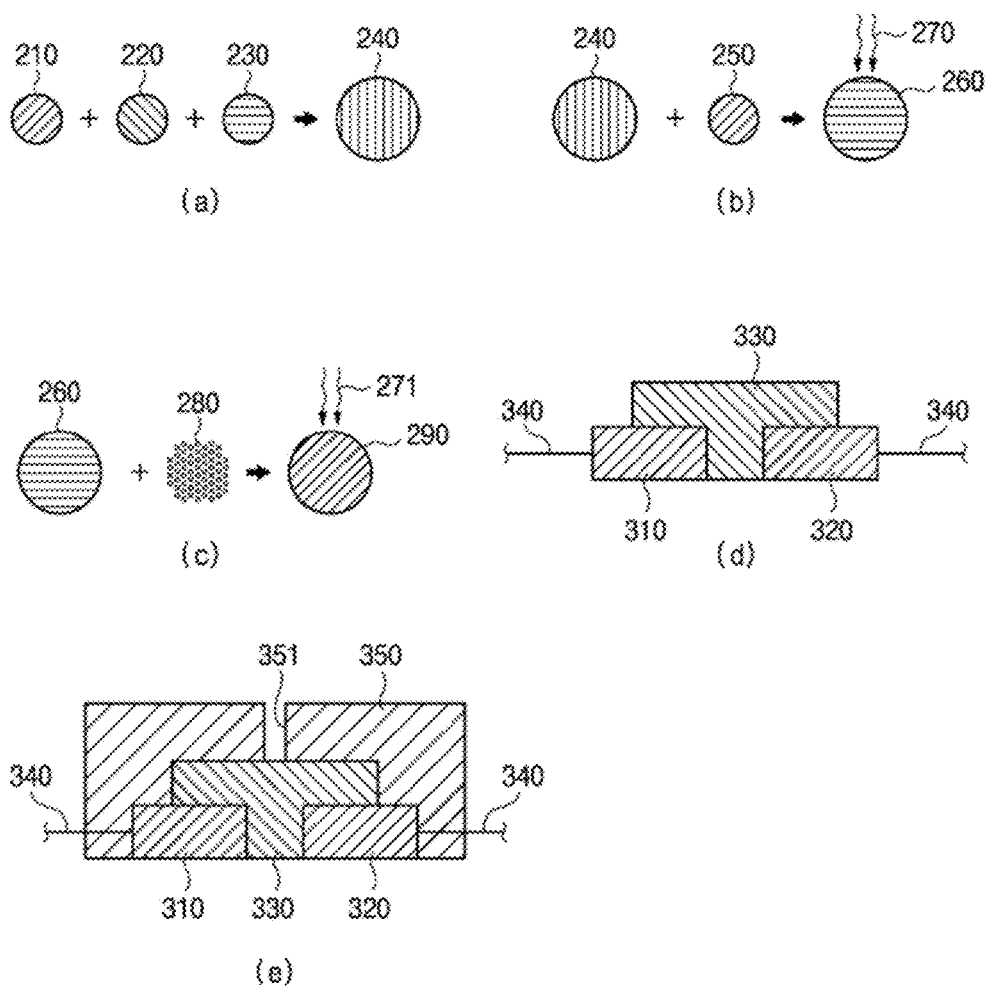

[FIG. 3]
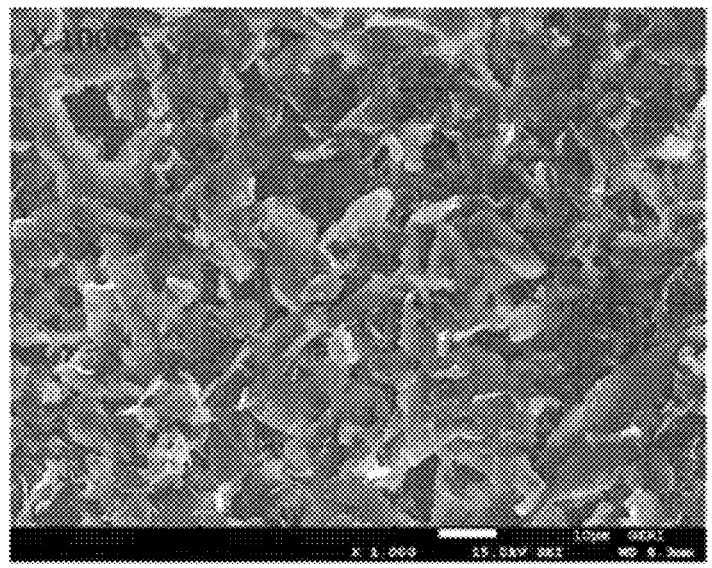
(a)
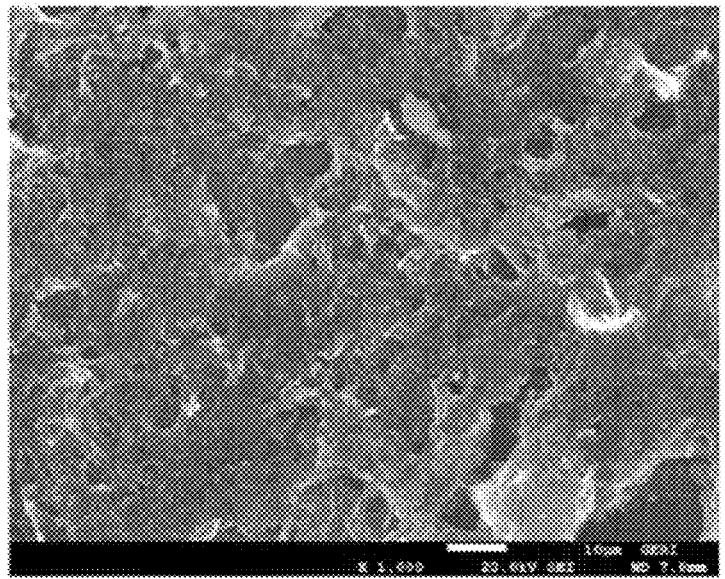
(b)

[FIG. 4]
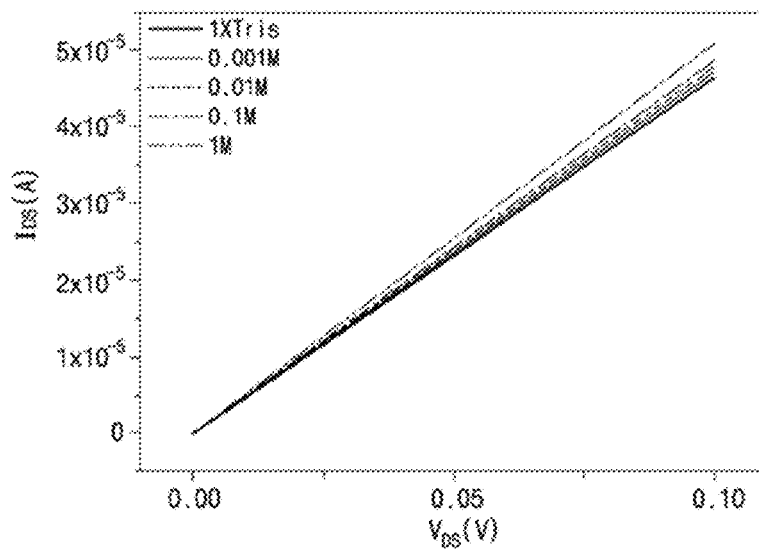
(a)
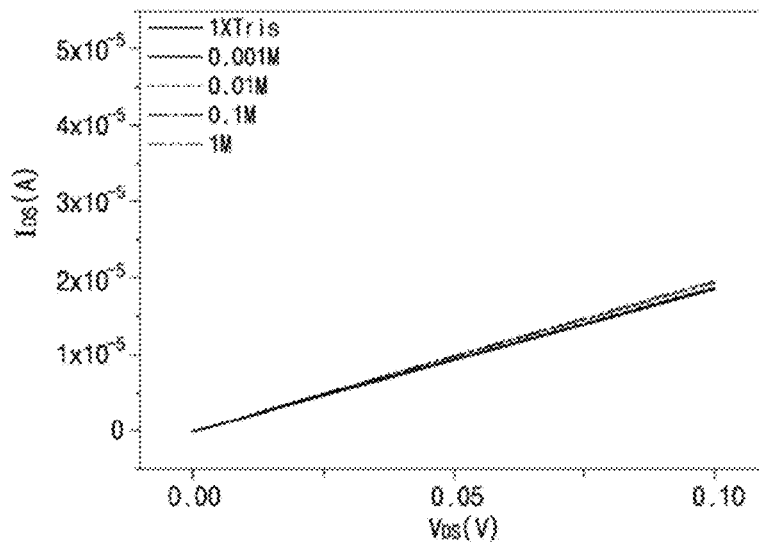
(b)

[FIG. 5]
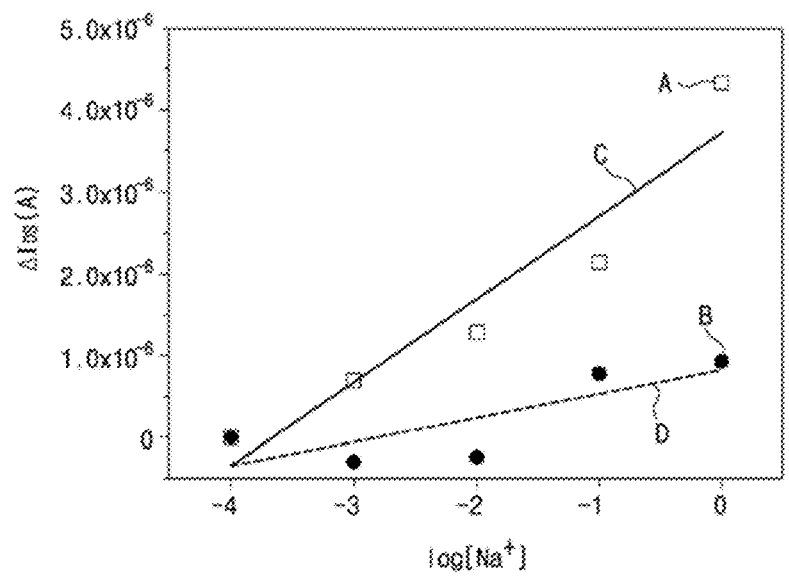
[FIG. 6]
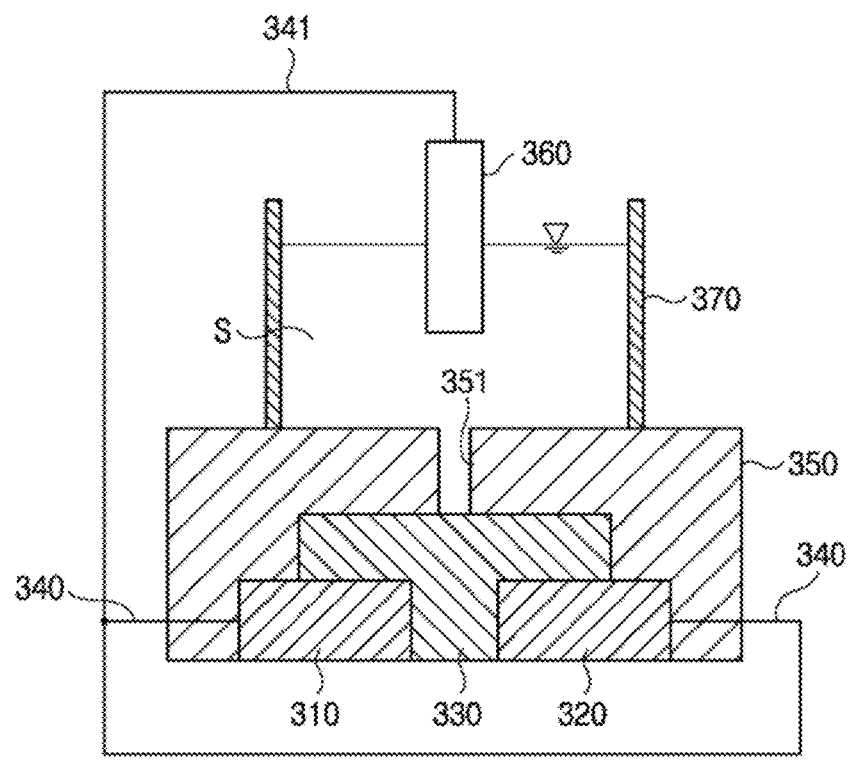

ION DETECTION SENSOR FABRICATION METHOD AND ION DETECTION SENSOR FABRICATED BY THE SAME

ACKNOWLEDGEMENTS

This research was supported by the projects as below.
[Project number] 53092048
[Ministry] Ministry of Small and Medium-sized Enterprises and Startups, Korea
[Management agency] Korea Institute for Advancement of Technology(KIAT)
[Program name] Regional Specialized Industry Development Plus Program(R&D)
[Project name] Development of high precision biosensor and system for detecting multiple target substance simultaneously
[Contribution ratio] 1/1
[Supervision institution] MCK Tech Co., Ltd.
[Period] 2021.04.01~2022.12.31

TECHNICAL FIELD

The present invention relates to an ion detection sensor fabrication method and an ion detection sensor fabricated by the same and, more particularly, to an ion detection sensor fabrication method that enables process streamlining and cost savings, and an ion detection sensor fabricated by the same.

BACKGROUND ART

Various ions, such as sodium ($Na^+$), potassium ($K^+$), calcium ($Ca^{2+}$), and chloride ($Cl^-$), are present in the human body and play a significant role in hormonal balance and physiology of the human body. Among others, sodium ions ($Na^+$) are essential for maintaining normal functions of the human body, such as transmission of nerve impulses and regulation of ion concentrations in the blood and cells. For example, the sodium ion concentration in the body is generally in the range of 135 mM to 145 mM. Incomplete excretion of sodium ions due to malfunction of the kidneys or long term intake of sodium ions in a dose exceeding a recommended daily allowance can cause ions in the body to be out of balance, which leads to hypernatremia ($\geq 145$ mM) or hyponatremia ($\leq 135$ mM). Excess or deficiency of ions other than sodium can also lead to abnormal symptoms in the body.

Ion levels in the body may be identified by testing ion levels in urine. Advantageously, urine can be easily collected from a subject without affecting their daily lives. However, a urine test method commonly used in hospitals is a 24-hour test that calculates the concentration of each ion distributed throughout the body through ion level measurement over 24 hours using a urine sample collected over 24 hours. However, such a 24-hour test costs lots of effort and is less reliable. Therefore, there is a need for a disposable sensor that is suitable for detection of $Na^+$ through a spot test without requiring collection of a urine sample over 24 hours.

The concentration of sodium ions in urine may be determined using various devices. For example, the sodium ion concentration in urine may be tested using an atomic absorption spectroscope, a neutron activation analyzer, a flame photometer, ion-sensitive electrodes (ISEs), ion-sensitive field-effect transistors (ISFETs), and the like. Atomic absorption spectroscopy, neutron activation analysis, and flame photometry can accurately detect sodium ions. However, these test methods have problems of necessity of a large scale device and professionals trained in handling such a device. In addition, despite the advantages of small size and high portability, ISEs have a problem of low measurement precision due to leakage of ions from an internal solution.

On the other hand, ISFETs allow quick and precise detection and low-cost mass production through a semiconductor manufacturing process and thus can be a suitable candidate for development of disposable sensors. However, ISFETs require a sensor fabrication process consisting of many steps, including sputtering, photolithography, dicing, and the like, which are accompanied by increase in equipment, manpower, and material costs. Accordingly, in order to achieve low-cost production of ISFETs, it is necessary to streamline the fabrication process.

As an example of the related art, there is Korean Patent Laid-open Publication No. 2015-0004254 (publication date: Jan. 12, 2015).

DISCLOSURE

Technical Problem

Embodiments of the present invention are conceived to solve such a problem in the art and are aimed at providing an ion detection sensor fabrication method that enables process streamlining and cost savings, and an ion detection sensor fabricated by the same.

It will be understood that objects of the present invention are not limited to the above and the above and other objects of the present invention will become apparent to those skilled in the art from the detailed description of the following embodiments in conjunction with the accompanying drawings.

Technical Solution

In accordance with one aspect of the present invention, an ion detection sensor fabrication method includes: preparing an ion-sensitive film preparation solution; preparing an ion-sensitive mixed layer preparation solution by mixing the ion-sensitive film preparation solution with graphene powder; and forming an ion-sensitive mixed layer sensitive to a target ion by applying the ion-sensitive mixed layer preparation solution to fill a gap between a source and a drain spaced apart from each other and to cover at least a portion of an upper surface of each of the source and the drain.

In one embodiment of the present invention, preparing the ion-sensitive film preparation solution may include preparing an ion-sensitive material by mixing an ionophore of the target ion with a plasticizer and a polymer as a base material, the plasticizer serving to improve lifespan, detection sensitivity, and detection limit of the ion-sensitive mixed layer.

In one embodiment of the present invention, preparing the ion-sensitive film preparation solution may further include dissolving the ion-sensitive material in a solvent to prepare the ion-sensitive film preparation solution.

In one embodiment of the present invention, in preparing the ion-sensitive mixed layer preparation solution, a composition ratio of the graphene powder to the polymer may range from 1:0.5 to 1:2.5.

In one embodiment of the present invention, preparing the ion-sensitive mixed layer preparation solution may include performing ultrasonication to disperse the mixed graphene powder.

In one embodiment of the present invention, the ion detection sensor fabrication method may further include, after preparing the ion-sensitive mixed layer, bonding a wire to the source and the drain to allow voltage to be applied between the source and the drain therethrough.

In one embodiment of the present invention, the ion detection sensor fabrication method may further include, after bonding the wire to the source and the drain, forming an encapsulation portion using an epoxy resin to cover and insulate the ion-sensitive mixed layer, the source and the drain from outside, wherein the encapsulation portion is formed therein with an ion detection channel into which a measurement solution containing the target ion is introduced to contact the ion-sensitive mixed layer.

In accordance with another aspect of the present invention, there is provided an ion detection sensor fabricated by the ion detection sensor fabrication method set forth above, wherein the ion detection sensor includes: the source and the drain spaced apart from each other; the ion-sensitive mixed layer filling a gap between the source and the drain while covering at least a portion of the upper surface of each of the source and the drain, wherein the ion-sensitive mixed layer is sensitive to the target ion; and a reference electrode at least partly contacting the measurement solution containing the target ion and contacting the ion-sensitive mixed layer.

Advantageous Effects

In the ion detection sensor fabrication method according to the embodiments of the present invention, the ion-sensitive mixed layer may be formed by application of the ion-sensitive mixed layer preparation solution through a simple printing process such as screen printing, inkjet printing, stencil printing, gravure printing, and flexographic printing, thereby allowing process streamlining and cost savings.

It will be understood that advantageous effects of the present invention are not limited to the above and include any advantageous effects conceivable from the features disclosed in the detailed description of the present invention or the appended claims.

DESCRIPTION OF DRAWINGS

FIG. 1 is a flowchart of an ion detection sensor fabrication method according to one embodiment of the present invention.

FIG. 2 is a schematic view illustrating the ion detection sensor fabrication method according to the embodiment of the present invention.

FIG. 3(a) is an image of reduced graphene oxide (rGO) and FIG. 3(b) is an image of an rGO-containing ion-sensitive mixed layer formed by the ion detection sensor fabrication method according to the embodiment of the present invention.

FIG. 4 shows graphs showing changes in current in an ion-sensitive mixed layer of the ion detection sensor fabricated by the ion detection sensor fabrication method according to the embodiment of the present invention depending on ion concentration and a graphene powder-to-polymer ratio.

FIG. 5 is a graph showing Na+ concentration-dependent changes in current in an ion-sensitive mixed layer of the ion detection sensor fabricated by the ion detection sensor fabrication method according to the embodiment of the present invention.

FIG. 6 is a schematic view of the ion detection sensor fabricated by the ion detection sensor fabrication method according to the embodiment of the present invention.

BEST MODE

Reference will now be made in detail to various embodiments, examples of which are illustrated in the accompanying drawings. It should be understood that the present invention may be embodied in different ways and is not limited to the following embodiments. In the drawings, portions irrelevant to the description will be omitted for clarity. Like components will be denoted by like reference numerals throughout the specification.

Throughout the specification, when an element or layer is referred to as being "on," "connected to," or "coupled to" another element or layer, it may be directly on, connected to, or coupled to the other element or layer or intervening elements or layers may be present. In addition, unless stated otherwise, the term "includes" should be interpreted as not excluding the presence of other components than those listed herein.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Hereinafter, embodiments of the present invention will be described with reference to the accompanying drawings.

FIG. 1 is a flowchart of an ion detection sensor fabrication method according to one embodiment of the present invention and FIG. 2 is a schematic view illustrating the ion detection sensor fabrication method according to the embodiment of the present invention.

Referring to FIG. 1 and FIG. 2, the ion detection sensor fabrication method may include an ion-sensitive film preparation solution preparation step S110, an ion-sensitive mixed layer preparation solution preparation step S120, and an ion-sensitive mixed layer forming step S130.

First, in the ion-sensitive film preparation solution preparation step S110, an ion-sensitive film preparation solution 260 is prepared. The ion-sensitive film preparation solution preparation step S110 may include an ion-sensitive material preparation step S111 and a dissolution step S112.

Referring to FIG. 2(a), in the ion-sensitive material preparation step S111, an ion-sensitive material 240 is prepared by mixing an ionophore 210 of a target ion to be detected from a measurement solution with a plasticizer 220 and a polymer 230.

The plasticizer 220 serves to increase lifespan of a finally obtained ion-sensitive mixed layer 330. In addition, the plasticizer 220 serves to improve detection sensitivity, detection limit, and selectivity for specific ions. The plasticizer 220 may be appropriately selected depending on the type of ionophore specific for the target ion. The polymer 230 may be used as a base material of the ion-sensitive material 240.

In the ion-sensitive material 240, the ionophore 210 may be present in an amount of 1% by weight (wt %) to 3 wt %, the plasticizer 220 may be present in an amount of 64 wt % to 66 wt %, and the polymer 230 may be present in an amount of 32 wt % to 34 wt %.

Next, referring to FIG. 2(b), in the dissolution step S112, the ion-sensitive material 240 is dissolved in a solvent 250 to prepare the ion-sensitive film preparation solution 260.

In the dissolution step (S112), agitation may be performed such that the ion-sensitive material 240 can be thoroughly dissolved in the solvent 250. Here, agitation may include mechanical agitation, such as vortexing, or ultrasonication 270.

When the target ion is Na$^+$, a sodium ionophore may be used as the ionophore 210. In addition, polyvinyl chloride or fluoropolysilicone may be used as the polymer 230. Further, tetrahydrofuran may be used as the solvent 250.

In the ion-sensitive mixed layer preparation solution preparation step S120, an ion-sensitive mixed layer preparation solution 290 is prepared by mixing the ion-sensitive film preparation solution 260 with graphene powder 280 (see FIG. 2(c)). When the ion-sensitive film preparation solution 260 is mixed with the graphene powder 280, the ion-sensitive material is formed around graphene.

The ion-sensitive mixed layer preparation solution preparation step S120 may include an ultrasonication step S121. In the ultrasonication step S121, ultrasonication 271 is performed to disperse the mixed graphene powder 280.

In the ion-sensitive mixed layer forming step S130, an ion-sensitive mixed layer 330 sensitive to the target ion is formed by applying the ion-sensitive mixed layer preparation solution 290 to fill a gap between a source 310 and a drain 320, which are spaced apart from each other, and to cover at least a portion of an upper surface of each of the source 310 and the drain 320 (see FIG. 2(d)).

The ion-sensitive mixed layer 330 containing the ionophore 210 may provide a membrane allowing selective transportation of specific ions therethrough, thereby enabling ion-specific detection. That is, various ion detection sensors can be implemented using ionophores 210 transporting specific ions.

In the ion-sensitive mixed layer forming step S130, the ion-sensitive mixed layer 330 may be formed by application of the ion-sensitive mixed layer preparation solution 290 through a simple printing process, such as screen printing, inkjet printing, stencil printing, gravure printing, and flexographic printing, thereby allowing process streamlining and cost savings.

The applied ion-sensitive mixed layer preparation solution 290 may be cured into the ion-sensitive mixed layer 330. Here, the ion-sensitive mixed layer 330 may form a channel between the source 310 and the drain 320.

FIG. 3(a) is an image of reduced graphene oxide (rGO) and FIG. 3(b) is an image of an rGO-containing ion-sensitive mixed layer fabricated by the ion detection sensor fabrication method according to the embodiment of the present invention.

As shown in FIG. 3(b), the reduced graphene oxide in the ion-sensitive mixed layer is wrapped by a polymer. The amount of the polymer wrapped around the graphene may vary depending on changes in content of the graphene powder in the ion-sensitive mixed layer, such that the ion-sensitive mixed layer can have increased sensitivity or selectivity to specific ions.

In the ion-sensitive mixed layer preparation solution preparation step S120, the graphene powder 280 and the polymer 230 may be mixed with each other in a predetermined ratio. Preferably, a ratio of the graphene powder 280 to the polymer 230 ranges from 1:0.5 to 1:2.5.

FIG. 4 shows graphs showing changes in current in the ion-sensitive mixed layer of the ion detection sensor fabricated by the ion detection sensor fabrication method according to the embodiment of the present invention depending on ion concentration and the graphene powder-to-polymer ratio. FIG. 4 shows results of observing ion concentration-dependent changes in $I_{DS}$-$V_{DS}$ with a voltage applied between a reference electrode and the source (VGS) fixed to zero. Specifically, FIG. 4(a) shows ion concentration-dependent changes in current in a graphene powder-to-polymer ratio of 1:2 and FIG. 4(b) shows ion concentration-dependent changes in current in a graphene powder-to-polymer ratio of 1:1.

From the results shown in FIG. 4(a) and FIG. 4(b), it can be seen that an increase rate of drain-source current ($I_{DS}$) with increasing drain-source voltage ($V_{DS}$), that is, a slope of a transfer characteristic curve ($I_{DS}$-$V_{DS}$), in a graphene powder-to-polymer ratio of 1:2 is greater than that in a graphene powder-to-polymer ratio of 1:1.

That is, referring to FIG. 4, it can be seen that the current increase rate increases with increasing graphene powder-to-polymer ratio. Accordingly, it can be seen that detection sensitivity increases with increasing content of graphene in the ion-sensitive mixed layer. However, considering that increase in graphene content can cause difficulty in controlling application of the ion-sensitive mixed layer preparation solution due to increase in viscosity of the ion-sensitive mixed layer preparation solution, it is desirable that the graphene-to-polymer ratio be set to 1:2.5 or less.

FIG. 5 is a graph showing Na$^+$ concentration-dependent changes in current ($I_{DS}$-$V_{DS}$) in the ion-sensitive mixed layer of the ion detection sensor fabricated by the ion detection sensor fabrication method according to the embodiment of the invention. In FIG. 5, reference symbol A denotes a variance of drain-source current ($I_{DS}$) depending on Na+ concentration in logarithmic scale in a graphene powder-to-polymer ratio of 1:2 and reference symbol B denotes a variance of drain-source current ($I_{DS}$) depending on Na+ concentration in logarithmic scale in a graphene powder-to-polymer ratio of 1:1. In addition, reference symbol C denotes a slope line indicating sensitivity at the values denoted by reference symbol A (Sensitivity: 3.7E−6 A/dec), that is, a ratio of variance of current to variance of Na+ concentration in logarithmic scale, and reference symbol D denotes sensitivity at the values denoted by reference symbol B (Sensitivity: 0.8E−6 A/dec).

Referring to FIG. 5, it can be seen that sensitivity of the ion-sensitive mixed layer in a graphene powder-to-polymer ratio of 1:2 is greater than that in a graphene powder-to-polymer ratio of 1:1. Since this means that a variance of current is proportional to an ion detection rate, it can be seen that the concentration of the target ion can be determined through measurement of current in the ion detection sensor.

Referring back to FIG. 1 and FIG. 2, the ion detection sensor fabrication method may further include a wire bonding step S140. In the wire bonding step S140, a wire 340 is bonded to the source 310 and the drain 320 to allow voltage to be applied between the source 310 and the drain 320 therethrough.

In addition, the ion detection sensor fabrication method may further include an encapsulation portion forming step S150.

The encapsulation portion forming step S150 may be performed after the wire bonding step S140. In the encapsulation portion forming step S150, an encapsulation portion 350 is formed using an epoxy resin to cover and insulate the ion-sensitive mixed layer 330, the source 310 and the drain 320 from outside.

The encapsulation portion 350 may be formed therein with an ion detection channel 351 into which a measurement solution containing a target substance is introduced to contact the ion-sensitive mixed layer 330. To this end, in the encapsulation portion forming step S150, the epoxy resin is not applied to a region corresponding to the ion detection channel 351.

FIG. 6 is a schematic view of an ion detection sensor fabricated by the ion detection sensor fabrication method according to the embodiment of the present invention.

Referring to FIG. 6, the ion detection sensor may include a source 310, a drain 320, an ion-sensitive mixed layer 330, and a reference electrode 360.

The source 310 and the drain 320 may be spaced apart from each other.

The ion-sensitive mixed layer 330 may fill a gap between the source 310 and the drain 320 while covering at least a portion of the upper surface of each of the source 310 and the drain 320. The ion-sensitive mixed layer 330 may be sensitive to a target ion.

The ion detection sensor may include an encapsulation portion 350. The encapsulation portion 350 may cover and insulate the ion-sensitive mixed layer 330, the source 310 and the drain 320 from outside. The encapsulation portion 350 may have an ion detection channel 351 therein such that a measurement solution S containing the target ion is introduced into the ion detection channel 351 from above the encapsulation portion 350 and contacts the ion-sensitive mixed layer 330.

The ion detection sensor may further include a chamber 370 housing the measurement solution S.

The reference electrode 360 may at least partially contact the measurement solution S and may be electrically connected to a wire 340 connected to the source 310 and the drain 320 through another wire 341.

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the invention. For example, components described as implemented separately may also be implemented in combined form, and vice versa.

The scope of the present invention is indicated by the following claims and all changes or modifications derived from the meaning and scope of the claims and equivalents thereto should be construed as being within the scope of the present invention.

INDUSTRIAL APPLICABILITY

Ion-sensitive field-effect transistors (ISFETs) for monitoring ion concentration in the body allow quick and precise detection and low-cost mass production through a semiconductor manufacturing process and thus are widely used as a disposable sensor. In particular, in the ion detection sensor fabrication method according to the present invention, the ion-sensitive mixed layer can be easily implemented through a simple printing process, thereby allowing process streamlining and cost savings. Thus, the ion detection sensor fabrication method according to the present invention and the ion detection sensor fabricated by the same have high industrial applicability.

The invention claimed is:

1. An ion detection sensor fabrication method comprising:
preparing an ion-sensitive film preparation solution;
preparing an ion-sensitive mixed layer preparation solution by mixing the ion-sensitive film preparation solution with graphene powder; and
forming an ion-sensitive mixed layer sensitive to a target ion by applying the ion-sensitive mixed layer preparation solution to fill a gap between a source and a drain spaced apart from each other and to cover at least a portion of an upper surface of each of the source and the drain.

2. The ion detection sensor fabrication method according to claim 1, wherein preparing the ion-sensitive film preparation solution comprises preparing an ion-sensitive material by mixing an ionophore of the target ion with a plasticizer and a polymer as a base material, the plasticizer serving to improve lifespan, detection sensitivity, and detection limit of the ion-sensitive mixed layer.

3. The ion detection sensor fabrication method according to claim 2, wherein preparing the ion-sensitive film preparation solution further comprises dissolving the ion-sensitive material in a solvent to prepare the ion-sensitive film preparation solution.

4. The ion detection sensor fabrication method according to claim 2, wherein, in preparing the ion-sensitive mixed layer preparation solution, a composition ratio of the graphene powder to the polymer ranges from 1:0.5 to 1:2.5.

5. The ion detection sensor fabrication method according to claim 1, wherein preparing the ion-sensitive mixed layer preparation solution comprises performing ultrasonication to disperse the mixed graphene powder.

6. The ion detection sensor fabrication method according to claim 1, further comprising, after preparing the ion-sensitive mixed layer,
bonding a wire to the source and the drain to allow voltage to be applied between the source and the drain therethrough.

7. The ion detection sensor fabrication method according to claim 6, further comprising, after bonding the wire to the source and the drain,
forming an encapsulation portion using an epoxy resin to cover and insulate the ion-sensitive mixed layer, the source and the drain from outside,
wherein the encapsulation portion is formed therein with an ion detection channel into which a measurement solution containing the target ion is introduced to contact the ion-sensitive mixed layer.

8. An ion detection sensor fabricated by the ion detection sensor fabrication method according to claim 1, the ion detection sensor comprising:
the source and the drain spaced apart from each other;
the ion-sensitive mixed layer filling a gap between the source and the drain while covering at least a portion of the upper surface of each of the source and the drain, wherein the ion-sensitive mixed layer is sensitive to the target ion; and
a reference electrode at least partly contacting the measurement solution containing the target ion and contacting the ion-sensitive mixed layer.

* * * * *